US009878968B2

(12) United States Patent
Porter et al.

(10) Patent No.: US 9,878,968 B2
(45) Date of Patent: Jan. 30, 2018

(54) XYLENE SEPARATION PROCESS

(71) Applicant: ExxonMobil Chemical Patents Inc., Baytown, TX (US)

(72) Inventors: John R. Porter, Lake City, MI (US); Michael W. Weber, Houston, TX (US); Gaurav Agrawal, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/455,502

(22) Filed: Mar. 10, 2017

(65) Prior Publication Data

US 2017/0305818 A1 Oct. 26, 2017

Related U.S. Application Data

(60) Provisional application No. 62/327,511, filed on Apr. 26, 2016.

(51) Int. Cl.
*C07C 7/13* (2006.01)
*B01D 15/18* (2006.01)

(52) U.S. Cl.
CPC ............ *C07C 7/13* (2013.01); *B01D 15/1835* (2013.01)

(58) Field of Classification Search
None
See application file for complete search history.

(56) References Cited

U.S. PATENT DOCUMENTS

| | | | | |
|---|---|---|---|---|
| 3,201,491 | A | 8/1965 | Stine et al. | |
| 3,761,533 | A | 9/1973 | Otani et al. | |
| 4,029,717 | A | 6/1977 | Healy et al. | |
| 5,470,464 | A * | 11/1995 | Priegnitz | B01D 15/1842 210/198.2 |
| 6,395,951 | B1 * | 5/2002 | Hamm | B01D 3/14 208/347 |
| 8,168,845 | B2 | 5/2012 | Porter et al. | |

(Continued)

FOREIGN PATENT DOCUMENTS

WO 2016/133589 8/2016

OTHER PUBLICATIONS

Kawajiri et al., "Optimization Strategies for Simulated Moving Bed and PowerFeed Processes", AIChE Journal, vol. 52, No. 4, Apr. 2006, pp. 1343-1350.

(Continued)

*Primary Examiner* — Tam M Nguyen

(57) ABSTRACT

A process is described for separating paraxylene from a multicomponent fluid mixture of $C_8$ aromatics. A mixture of $C_8$ aromatics is fed to a simulated moving bed adsorptive apparatus having at least two sieve chambers and at least two rotary valves. Each sieve chamber may be operated individually using the PowerFeed process. The flow rates of the streams to or from the individual sieve chambers may be varied during the step time in an inverse manner such that a substantially constant flow to and from the apparatus is achieved. Alternatively, the flow rates to each sieve chamber may vary during the step time according to the same profile, but the rotary valves may be off-set and step independently in a staggered manner to achieve a substantially constant flow of a stream to or from the apparatus.

25 Claims, 4 Drawing Sheets

(56) References Cited

U.S. PATENT DOCUMENTS

| | | | | |
|---|---|---|---|---|
| 8,529,757 | B2 | 9/2013 | Go et al. | |
| 2010/0125163 | A1* | 5/2010 | Porter | B01D 15/1835 585/822 |
| 2013/0158330 | A1 | 6/2013 | Corradi | |
| 2013/0233698 | A1* | 9/2013 | Corradi | B01D 3/143 203/41 |
| 2016/0145174 | A1* | 5/2016 | Porter | B01D 15/1807 585/828 |

OTHER PUBLICATIONS

Minceva et al., “Modeling and Simulation of a Simulated Moving Bed for the Separation of p-Xylene,” Ind. Eng. Chem. Res., 2002, vol. 41, pp. 3454-3461.

Zhang et al., “PowerFeed Operation of Simulated Moving Bed Units: Changing Flow-Rates During the Switching Interval”, Journal of Chromatography A, vol. 1006, 2003, pp. 87-99.

* cited by examiner

XYLENE SEPARATION PROCESS

The present application claims the benefit of and priority to Provisional Application No. 62/327,511, filed Apr. 26, 2016 the entire contents of which are incorporated herein by reference.

TECHNICAL FIELD

This disclosure relates to a process for separating paraxylene from a multicomponent fluid mixture of $C_8$ aromatics, and more particularly to a process for separating paraxylene from such a fluid mixture with a simulated moving bed adsorption apparatus.

BACKGROUND

Of the three xylene isomers, paraxylene is the most commercially valuable. However, due to the similarity of their boiling points, adsorption is a commonly used method to separate paraxylene from the other xylene isomers, in which an adsorbent solid that preferentially adsorbs paraxylene over metaxylene and orthoxylene is used. Simulated moving bed (SMB) separation is especially useful for separating paraxylene from a mixture of $C_8$ aromatics.

A commercial embodiment of a simulated moving bed adsorption apparatus is used in the well-known Parex™ Process, which is used to separate $C_8$ aromatic isomers and provide a more highly pure paraxylene (PX) stream from a less highly pure mixture. See by way of example U.S. Pat. Nos. 3,201,491; 3,761,533; and 4,029,717. Other embodiments involving a simulated moving bed adsorption apparatus include the commercially available ELUXYL® and AROMAX® processes.

In a Parex™ unit, the locations of liquid input and output are moved by a fluid directing device described herein as a rotary valve device. This device may comprise one or more rotary valves, as well as various control and accessory means, such as inlet lines, outlets lines and valves associated therewith. The rotary valve device works in conjunction with conduits located between the adsorbent beds. The rotary valve device accomplishes moving the input and output locations through first directing the liquid introduction or withdrawal lines to specific conduits in fluid communication with particular adsorbent beds. After a specified time period, called the step time herein, the rotary valve device advances one index and redirects the liquid inputs and outputs to the conduit immediately adjacent and downstream of the previously used conduits. Each advancement of the rotary valve device to a new position is generally called a valve step, and the completion of all the valve steps is called a valve cycle. The step time is uniform for each valve step in a valve cycle, and may be from about 30 seconds to 4 minutes.

An example of a simulated moving bed adsorption apparatus contains 24 adsorbent beds and 24 conduits individually connected to a bed and providing fluid communication with the rotary valve device. The conduits of the adsorption apparatus may function, over time, as at least two liquid input lines (e.g., a feed input line and a desorbent input line) and two liquid output lines (e.g., an extract withdrawal line and a reformate withdrawal line).

In some simulated moving bed systems, a second rotary valve is used in parallel to allow for extra capacity or improve continuity of operations. A system with two rotary valves is described in U.S. Pat. No. 8,168,845.

In standard simulated moving bed separation processes, the flow rate of streams into and out of the simulated moving bed are held constant during the step time. However, modulation of flow during the step time has been found to enhance separation in certain instances involving simulated moving bed separation of fructose and glucose or separation of 1,1'-bi-2-naphthol enantiomers. The enhanced separation may result in greater purity of product streams or less desorbent use. This process for modulating flow rates during a step time has been referred to as a PowerFeed process. Examples of PowerFeed processes are described in an article by Kawajiri et al., "Optimization strategies for simulated moving bed and PowerFeed processes", AIChE J. Vol. 52 (2006) B, pp. 1343-1350, and in an article by Zhang et al., "PowerFeed operation of simulated moving bed units: changing flow-rates during the switching interval", Journal of Chromatography A, Vol. 1006, pp. 87-99, 2003, Elsevier B.V.

International Application publication No. WO 2016/133589 discloses a PowerFeed process, in which the flow rate of feed to the simulated moving bed apparatus is varied during each interval to enhance the separation of paraxylene from the multicomponent mixture. A challenge of using a PowerFeed process is that it requires larger and higher capacity peripheral equipment, such as attendant distillation towers, pumps, surge vessels, and heat exchangers, in order to handle the cyclic flows and much higher peak flow rate of streams as compared with a non-PowerFeed process where the flow rates remain constant, increasing cost and energy consumption. In addition, a PowerFeed process may have a high frequency of flow variation, which can accelerate wear and tear of peripheral equipment.

Thus, there is a need to further improve the PowerFeed mode of operation in a simulated moving bed adsorption process in a way that can make the process more efficient, minimize the size and/or complexity of peripheral equipment, and prolong the life cycle of peripheral equipment. Also, there is need for a PowerFeed process that can be easily implemented on existing facilities without significant modifications to the peripheral equipment, thereby minimizing capital investment.

BRIEF SUMMARY

Embodiments disclosed herein are directed to using an improved PowerFeed process to separate a $C_8$ aromatic, such as paraxylene or ethylbenzene, from a mixture of $C_8$ aromatics in a simulated moving bed adsorption apparatus having at least two sieve chambers and at least two rotary valves. The use of PowerFeed significantly enhances the separation of paraxylene (or other desired $C_8$ aromatic). When a simulated moving bed adsorption apparatus having two or more sieve chambers and two or more rotary valves is used, each sieve chamber may be operated individually, i.e., as two or more independent simulated moving bed units rather than a collective unit, using the PowerFeed process. Managing the PowerFeed process in each chamber such that a substantially constant flow rate of streams to or from the apparatus is achieved minimizes the size and complexity of the peripheral equipment, e.g., pumps, surge vessels, heat exchangers, conduits for transferring streams to and from the rotary valves, etc. Accordingly, the present invention reduces operation cost and energy consumption and prolongs the life cycle of the apparatus as compared to PowerFeed processes described in prior art. Embodiments disclosed herein allow for upgrading an existing simulated moving bed apparatus to use the PowerFeed process with minimized capital investment.

In one aspect, paraxylene is separated from a $C_8$ aromatic mixture by a simulated moving bed adsorption apparatus comprising at least a first sieve chamber and a second sieve chamber, each sieve chamber comprising multiple adsorbent beds. A feed stream of the mixture is split into a first feed sub-stream and a second feed sub-stream, and a desorbent stream is split into a first desorbent sub-stream and a second desorbent sub-stream. The first feed sub-stream and first desorbent sub-stream is introduced into the first sieve chamber, and the second feed sub-stream and second desorbent sub-stream is introduced into the second sieve chamber. A first extract sub-stream and a first raffinate sub-stream are withdrawn from the first sieve chamber, and a second extract sub-stream and a second raffinate sub-stream are withdrawn from the second sieve chamber. The first and the second extract sub-streams, each comprising paraxylene and desorbent, are combined to form an extract stream, and the first and second raffinate sub-streams, each comprising non-paraxylene $C_8$ aromatics and desorbent, are combined to form a raffinate stream. The flows of the first feed sub-stream, first desorbent sub-stream, first extract sub-stream, and first raffinate sub-stream to or from the first sieve chamber are controlled by a first rotary valve, and the flows of the second feed sub-stream, second desorbent sub-stream, second extract sub-stream, and second raffinate sub-stream to or from the second sieve chamber are controlled by a second rotary valve. Throughout the process, the flow is maintained through the first sieve chamber, and the flow is maintained through the second sieve chamber, but there is no fluid communication between the first and second sieve chambers.

The location of sub-streams into and out of the first sieve chamber and second sieve chamber are switched to a bed downstream in terms of the direction of the circulating fluid after a step time X. During the step time X, the flow rate of at least one pair of streams selected from the first and second feed sub-streams, first and second desorbent sub-streams, first and second extract sub-streams, and first and second raffinate sub-streams to or from the first and second sieve chambers are varied. The flow rate of the first sub-stream is varied according to a first flow rate profile, and the flow rate of the second sub-stream is varied according to a second flow rate profile, in a balanced manner such that the flow rate of the feed stream, desorbent stream, extract stream, and raffinate stream to and from the simulated moving bed adsorption apparatus is substantially constant. In one embodiment, the first and second flow rate profiles have an inverse relationship. In another embodiment, the first and second flow rate profiles are the same, the flow rate of at least one of the pair of streams selected from the first and second feed sub-streams, first and second desorbent sub-streams, first and second extract sub-streams, and first and second raffinate sub-streams to or from the first and second sieve chambers is changed after a subinterval X' of step time X, and the first rotary valve and second rotary valves are off-set by the subinterval X' and step in a staggered manner.

These and other objects, features, and advantages will become apparent in the following detailed description, drawings, specific embodiments, experiments, and accompanying claims.

DETAILED DESCRIPTION

Figure 1:
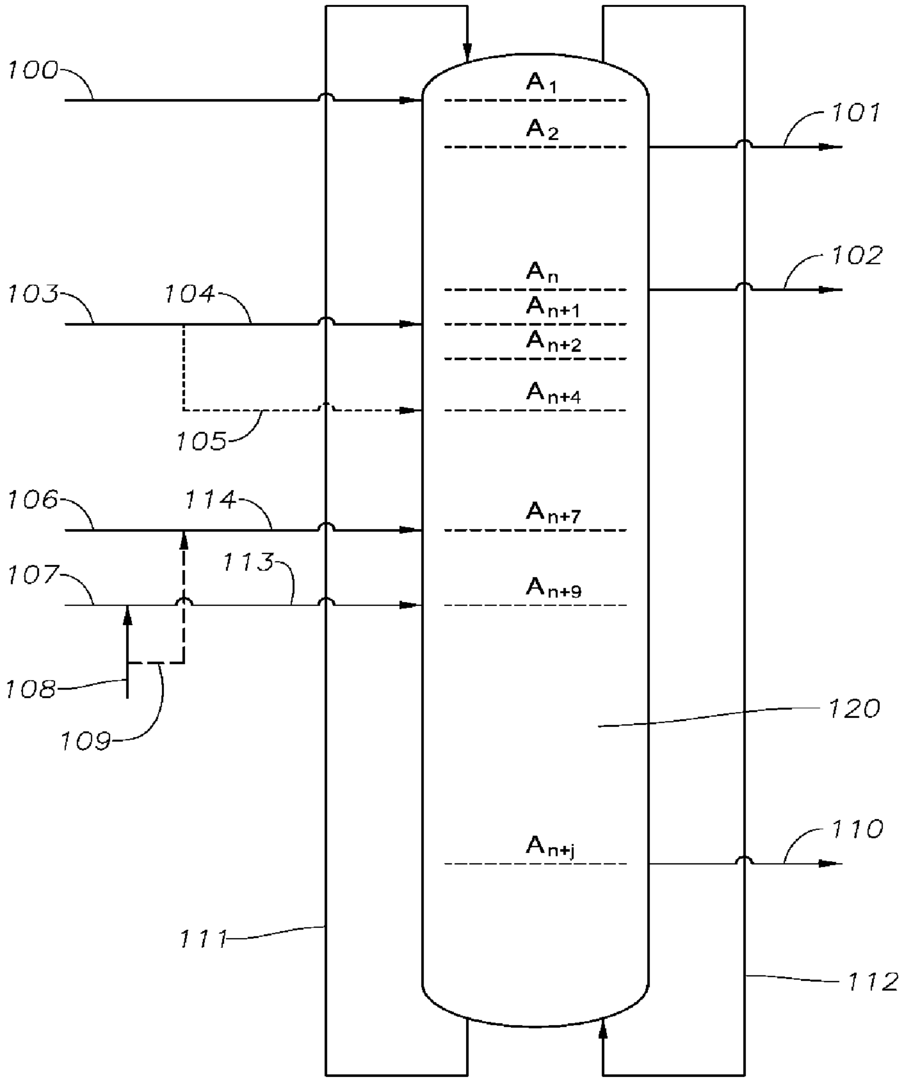
FIG. 1 is a schematic illustration of a simulated moving bed adsorptive separation system.

Embodiments disclosed herein are directed to using an improved PowerFeed process to separate a $C_8$ aromatic, such as paraxylene or ethylbenzene, from a mixture of $C_8$ aromatics in a simulated moving bed adsorption apparatus having at least two sieve chambers and at least two rotary valves. When a simulated moving bed adsorption apparatus having two or more sieve chambers and two or more rotary valves is used, each sieve chamber may be operated individually, i.e., as two or more independent simulated moving bed units rather than a collective unit, using the PowerFeed process. The flow rates of the streams to or from the individual sieve chambers may be varied during the step time in an inverse manner such that a substantially constant flow to and from the apparatus is achieved. Alternatively, the flow rates to each sieve chamber may vary during the step time according to the same profile, but the rotary valves may be off-set and step independently in a staggered manner to achieve a substantially constant flow of a stream to or from the apparatus.

The use of PowerFeed significantly enhances the separation of paraxylene (or other desired $C_8$ aromatic). Managing the PowerFeed process in each chamber such that a substantially constant flow rate of streams to or from the apparatus is achieved minimizes the size and complexity of the peripheral equipment, e.g., pumps, surge vessels, heat exchangers, conduits for transferring streams to and from the rotary valves, etc. Accordingly, embodiments disclosed herein reduce operation cost and energy consumption and prolongs the life cycle of the apparatus as compared to PowerFeed processes described in prior art. The disclosed embodiments allow for upgrading of existing simulated moving bed apparatuses to use the PowerFeed process with minimized capital investment.

Various terms used in this description will be understood in the context of this description. A further explanation of certain terms used herein is provided below.

$C_8$ aromatics are aromatic compounds having 8 carbon atoms. Examples of $C_8$ aromatics include paraxylene, metaxylene, orthoxylene and ethylbenzene.

Equilibrium xylene is a mixture of $C_8$ aromatics having a thermodynamic equilibrium concentration of the various $C_8$ aromatic compounds when the $C_8$ aromatics are subjected to non-selective isomerization conditions. Equilibrium xylene may be produced in a non-selective process for producing xylenes. A non-selective process for producing xylenes may involve reacting reactants over a non-selective catalyst. A non-selective process for producing xylenes is a process which produces equilibrium xylenes. A non-selective process for producing xylenes may take place over a non-selective catalyst. Examples of non-selective catalysts include large pore zeolites, such as zeolite X and zeolite Y, or amorphous aluminosilicates. When toluene is disproportionated over a large pore size zeolite, equilibrium zeolites may be produced. Equilibrium xylene may be produced, for example, in a xylene isomerization process, a transalkylation process or a reforming process. Equilibrium xylene may also be produced by other processes. Equilibrium xylene may comprise, for example, about 23 percent paraxylene, based on the total of the xylenes.

Enhanced paraxylene is a mixture of $C_8$ aromatics having a greater concentration of paraxylene than equilibrium xylene. Enhanced paraxylene may be produced in a selective process for producing xylenes. A selective process for producing xylenes may involve reacting reactants over a selective catalyst. Enhanced paraxylene may be produced, for example, by a selective toluene disproportion process or a selective toluene alkylation process. Enhanced paraxylene may also be produce by other processes. Enhanced paraxylene may have a concentration of, for example, at least 75% paraxylene, based on the total of $C_8$ aromatics.

A circulating fluid is the fluid (e.g. liquid) which flows in a continuous manner through a simulated moving bed adsorption apparatus. The concentration of compounds in the circulating fluid changes as the fluid flows through the apparatus due to, inter alia, adsorption and desorption of xylenes, ethylbenzene and desorbent, withdrawal of fluids in extract and reformate streams, and introduction of fluids through feed, desorbent and flush streams.

A rotary valve device is a device comprising at least one rotary valve. The rotary valve device may comprise various control and accessory means, such as inlet lines, outlet lines and valves associated therewith. In this description, rotary valve will be used to illustrate the disclosed embodiments, however, as would be known by one of skill in the art, any other liquid distribution device which distributes the flow of stream into and out of a simulated moving bed adsorptive device will be applicable in the disclosed embodiments. Other liquid distribution device may comprise a system of other types of valves, such as the system used in the ELUXYL® process.

A simulated moving bed adsorption apparatus of the disclosed embodiments comprises at least two adsorptive sieve chambers, each comprising beds of adsorbent stacked in at least one column. In operative use of the adsorption apparatus, in each sieve chamber, the beds are connected in a fluid and circular manner in series with one another.

A simulated countercurrent absorptive separation is a separation which takes place in a simulated moving bed adsorption apparatus.

A sieve chamber is an apparatus having adsorbent beds stacked one on top of the other. A simulated moving bed adsorption apparatus according to the disclosed embodiments can comprise at least two sieve chambers, for example, two, three, four, five, and six sieve chambers in some embodiments.

An adsorbent bed is a bed of adsorbent. A sieve chamber includes multiple adsorbent beds. Any fluid in an adsorbent bed, whether or not adsorbed on an adsorbent, is considered to be part of the bed. Accordingly, when fluid is introduced into or withdrawn from an adsorbent bed, the fluid is considered as being introduced or withdrawn, into or from the bed itself.

An adsorbent is a solid material, which selectively adsorbs one $C_8$ aromatic, for example paraxylene, in preference to other $C_8$ aromatics, for example metaxylene, orthoxylene and ethylbenzene. In a simulated moving bed apparatus, such as a Parex™ unit, examples of adsorbents include charcoal, ion-exchange resins, silica gel, activated carbon, zeolitic material, and the like. An adsorbent, which is particularly useful for separating paraxylene from other $C_8$ aromatics, is a faujasite-type molecular sieve material, such as zeolite X or zeolite Y, optionally, substituted or treated with an enhancing agent, such as a Group I or II element, such as potassium or barium. Examples of adsorbents for separating paraxylene from other $C_8$ aromatics can be those as described in U.S. Pat. No. 3,761,533, content of which are incorporated herein by reference.

A sorbate is a compound, which is adsorbed on an adsorbent or desorbed from an adsorbent. In a Parex™ process for separating paraxylene from $C_8$ aromatic mixtures, sorbates include xylenes, ethylbenzene and desorbents.

Sorbate affinity is the tendency of a sorbate, such as a paraxylene, to be adsorbed by an adsorbent. In a paraxylene separation process, paraxylene has a greater sorbate affinity to the adsorbent than other $C_8$ aromatics. Also, ethylbenzene may have a greater sorbate affinity to the adsorbent than either metaxylene or orthoxylene.

Adsorbent selectivity is the tendency of an adsorbent to adsorb a particular sorbate from a mixture of sorbates. In a paraxylene separation process, the adsorbent will adsorb paraxylene at a faster rate than other $C_8$ aromatics. The adsorbent may also adsorb ethylbenzene at a faster rate than either metaxylene or orthoxylene.

A desorbent is a liquid, which displaces $C_8$ aromatics from adsorbent. The desorbent may be equally or slightly more preferentially adsorbed on the adsorbent than paraxylene. The desorbent may have a greater sorbate affinity for the adsorbent than other $C_8$ aromatics. The desorbent should have a boiling point significantly different than the boiling points of $C_8$ aromatics, such that the desorbent may be separated from $C_8$ aromatics by distillation. Examples of desorbents for a paraxylene separation process include paradiethylbenzene and toluene.

Unless otherwise specified herein, the terms, downstream and upstream, refer to the direction of flow of circulating fluid.

A number of abbreviations are used herein. PX stands for paraxylene. MX stands for metaxylene. OX stands for orthoxylene. EB stands for ethylbenzene. PDEB stands for paradiethylbenzene. TOL stands for toluene. NA stands for non-aromatics. Non-aromatics, such as paraffins, may be introduced into an adsorption apparatus as a feed impurity, especially when the feed comprises $C_8$ aromatics obtained from a reforming process.

A system employing a simulated countercurrent flow process such as described in U.S. Pat. Nos. 3,201,491; 3,761,533; 4,029,717; and 8,529,757 are shown in FIG. 1, along with several modifications. The diagram in FIG. 1 will be understood by those having ordinary skill in the art to depict a simulated moving bed process. Desorbent is introduced through conduit 100. Liquid withdrawal stream leaves the apparatus through conduit 101. Extract (containing the desired product) leaves the apparatus via conduit 102. Raffinate leaves the apparatus through conduit 110. The secondary flush is added through conduit 103. The primary flush is added through conduit 106. A $C_8$ aromatic feed, which comprises 15 to 30 volume percent paraxylene, is added to the apparatus through conduit 107. Optionally, a $C_8$ aromatic mixture, which comprises 75 to 98 volume percent paraxylene, is added as an additional feed through conduit 108. Optionally, a $C_8$ aromatic mixture, which comprises 80 to 95 volume percent paraxylene is added as a portion of the primary flushing medium through conduit 109.

Not shown in the drawing, but as would be recognized by one of skill in the art in possession of the disclosure of U.S. Pat. No. 8,529,757, is one or more distillation towers and attendant pumps and conduits, which may be utilized to purify the liquid withdrawal stream leaving the above-described apparatus via conduit 101. However, such down-stream operations can be minimized or entirely omitted by rerouting (such as by replumbing or retrofitting) the liquid withdrawal stream from conduit 101 to conduit 103. In this way, the liquid withdrawal stream from conduit 101 is used as the secondary flush medium, which is introduced into the apparatus through conduit 103.

Continuing with the description of FIG. 1, the arrow 112 represents the simulated movement of beds upward through apparatus 120 containing plural adsorption beds $A_1$ through $A_{n+j}$. Arrow 111 represents the countercurrent flow of circulating fluid to the adsorbent beds. In operation, the adsorbent does not flow, but the various inlet and outlet streams, such as feed, product and flush streams, cycle through the adsorbent beds, represented by beds $A_1$ through $A_{n+j}$, in a direction, which is countercurrent to the simulated movement of adsorbent beds and concurrent to the direction of the circulating fluid. This simulates the movement of the adsorbent beds $A_1$ through $A_{n+j}$. Theoretically, there may be any number of adsorbent beds, thus n>2 and n+j is the maximum number of adsorbent beds. However, from a practical standpoint the number of bed lines is limited by design considerations and other factors. It will be understood that n and j are positive integers and that in an example of a commercial embodiment the total number of adsorbent beds is 24, and thus n+j typically may be 24. Certain adsorbent beds, i.e., beds between $A_2$ and $A_n$, beds $A_{n+3}$, $A_{n+5}$, $A_{n+6}$, and $A_{n+10}$ through $A_{n+j-1}$ are not depicted in FIG. 1, for convenience of view. The adsorbent beds may be contained within a single sieve chamber as shown in FIG. 1, or may be split between multiple sieve chambers connected to each other by conduits.

In the unit shown in FIG. 1, xylene and ethylbenzene molecules from feed 107 are adsorbed in bed $A_{n+9}$. As the adsorbent in bed $A_{n+9}$ becomes saturated with $C_8$ aromatics, a portion of the $C_8$ aromatics in the feed flow along with circulating fluid and flow into at least one bed, such as $A_{n+10}$ (not shown in FIG. 1), below bed $A_{n+9}$. According to a predetermined cycle time, the flow of feed, along with the flows of other inlet and outlet streams, is shifted to one adsorbent bed below. In FIG. 1 the bed below $A_{n+9}$ would be bed $A_{n+10}$ (not shown in FIG. 1). The direction of the shifting of feed and other streams to and from the adsorbent apparatus is the same as the direction of the flow of the circulating fluid through the apparatus. This shifting of streams results in adsorbed $C_8$ aromatics being moved (in a simulated manner) to beds above the bed to which feed is being introduced at any given time.

The feed which is introduced through conduit 107 may comprise equilibrium xylenes (such as from a powerformer, isomerization unit or transalkylation unit). Such equilibrium xylenes may comprise about 21-24 wt % paraxylene (PX). A portion of the feed introduced through conduit 107, may also comprise enhanced paraxylene, for example, from a selective toluene disproportionation unit (STDP unit), selective benzene or toluene methylation unit, or selective process for converting methanol to paraxylene. This enhanced paraxylene may comprise, for example, about 85-90 wt % PX.

The paraxylene is desorbed from adsorbent in the beds by desorbent, which is introduced into bed $A_1$ of the adsorption apparatus through conduit 100. The desorbent displaces paraxylene from the adsorbent. The desorbent also has a different boiling point than the $C_8$ aromatics and is easily separated from $C_8$ aromatics in a distillation process. Examples of desorbent include paradiethylbenzene (PDEB), toluene (TOL), tetralin, or a mixture thereof.

An extract stream is withdrawn from bed $A_n$ through conduit 102. The extract stream comprises a mixture of the purified paraxylene and the desorbent. As shown in FIG. 1, the withdrawal point of the extract stream though conduit 102 is between the point of introduction of the feed through conduit 107 and the point of introduction of the desorbent through conduit 100. A raffinate stream is withdrawn from bed $A_{n+j}$ through conduit 110. The raffinate stream comprises paraxylene-depleted $C_8$ aromatics and desorbent.

In view of the configuration of the simulated moving bed process, the various feeds and products must share the conduits between the adsorbent beds and the liquid distribution device (not shown). To prevent contamination of the extract stream with residual metaxylene, orthoxylene and ethylbenzene from the residue of feed stream in the conduit, the conduit is flushed in two stages with first a primary medium and second with a secondary flush medium. Liquid which is optionally withdrawn through conduit 101 may either be sent to the extract tower for recovery or recycled and used for primary flush through conduit 106 or secondary flush through conduit 104.

A first or primary flushing medium is introduced into conduit 106, including a terminal portion 114 of this conduit, which is connected to adsorbent apparatus 120. In FIG. 1, the primary flush fluid displaces residual feed in the conduit at the location of bed $A_{n+7}$, which is two beds above (i.e., two beds upstream, in terms of the direction of circulating fluid) bed $A_{n+9}$ into which feed is introduced via conduit 107. Although not shown in FIG. 1, it will be understood that conduit 106 may be connected to beds located further away, e.g., bed $A_{n+6}$, or closer, e.g., bed $A_{n+8}$, than bed $A_{n+7}$. The primary flushing medium may comprise one or more components. When the primary flushing medium comprises two components, these components may be, for example, a non-$C_8$ aromatic, such as desorbent, and a $C_8$ aromatics mixture, comprising, for example, from 80 to 95 volume percent paraxylene. These components may be mixed upstream of a rotary valve device (not shown in FIG. 1) and passed together through the rotary valve device into conduit 106. In another embodiment, these components may be passed sequentially into conduit 106. For example, the $C_8$ aromatics mixture, comprising from 80 to 95 volume percent paraxylene, may be passed first through a rotary valve device into conduit 106, followed by introducing desorbent component through the rotary valve device and into conduit 106. In another embodiment, at least a portion of the $C_8$ aromatics mixture, comprising from 80 to 95 volume percent paraxylene, may be passed directly to the terminal portion 114 of conduit 106 through conduit 109. A portion of the $C_8$ aromatics mixture, comprising from 80 to 95 volume percent paraxylene, may also be introduced into a terminal portion 113 of conduit 107 via conduit 108 and introduced as feed to bed $A_{n+9}$. In another embodiment at least a portion of the $C_8$ aromatics mixture, comprising from 80 to 95 volume percent paraxylene, may be combined with a different $C_8$ aromatics mixture, comprising from 15 to 30 volume percent paraxylene, and this combined $C_8$ aromatic mixture may be passed through a rotary valve device (not shown in FIG. 1) into conduit 107.

As shown in FIG. 1, a second or secondary flushing medium is introduced into conduit 103, including a terminal portion 104 of this conduit, which is connected to adsorbent apparatus 120. In FIG. 1, the secondary flush fluid displaces residual primary flush fluid in the conduit at the location of bed $A_{n+1}$, which is six beds above (i.e., six beds upstream, in terms of the direction of circulating fluid) bed $A_{n+7}$ into which primary flush fluid is introduced and one bed below bed $A_n$ from which an extract stream is withdrawn via conduit 102. However, it will be understood that the flow of secondary flush fluid through conduit 103 may be diverted to a bed located further away from bed $A_n$ and closer to bed $A_{n+7}$. In FIG. 1, this diversion of flow is shown by conduit 105, which is connected to bed $A_{n+4}$. When the secondary flush medium comprises little or no metaxylene, orthoxylene and ethylbenzene, the secondary flush medium and the residue of primary flush medium in the conduit comprises little or no metaxylene, orthoxylene and ethylbenzene, the secondary flush medium may flow towards a bed located close (e.g., one bed away) to the extract withdrawal point. When the secondary flushing medium and the residue of the primary flushing medium in the conduit are such that significant quantities of metaxylene, orthoxylene and especially ethylbenzene are introduced, the bed, to which the secondary flushing medium is directed, the location of the secondary flush step should be further away from the extract point to allow sufficient separation of paraxylene from the other $C_8$ aromatics.

Again, it should be emphasized, as would be known by one having ordinary skill in the art that these positions are relative and that, although the actual positions change by virtue of the movement of the rotary valve (not shown), the relative positions of the conduits remains the same. Thus, it will be understood by one of ordinary skill in the art that FIG. 1 depicts a simplified simulated moving bed apparatus with a rotary valve, wherein countercurrent "movement" of the solids in beds $A_1$ through $A_{n+j}$ relative to the fluid streams is simulated by the use of the rotary valve, which is not shown in the FIG. 1. Also, the beds $A_1$ through $A_{n+j}$ may be split between two or more sieve chambers and additional rotary valves may be used to increase the throughput to the beds.

Figure 2:
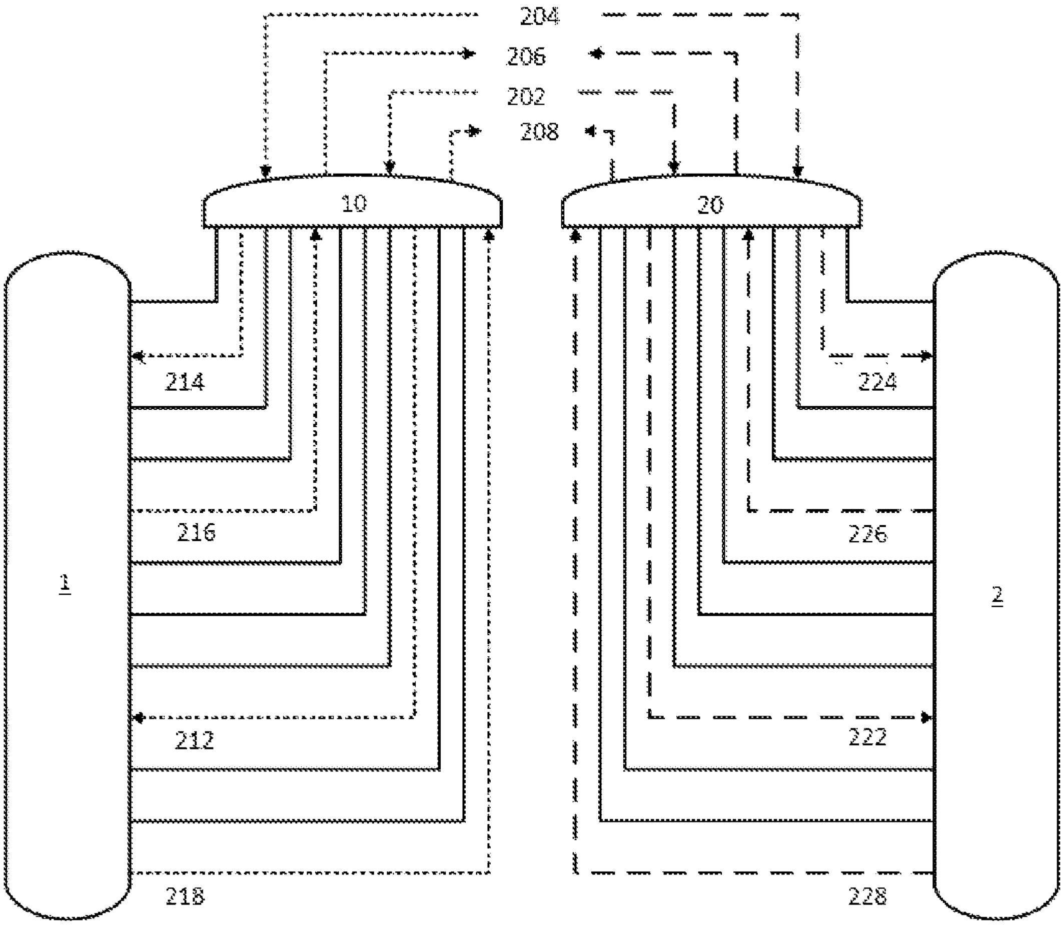
FIG. 2 shows a schematic illustration of the simulated moving bed adsorption apparatus comprising two sieve chambers according to at least some embodiments disclosed herein.

A simulated moving bed adsorption apparatus according to the present invention comprises two or more sieve chambers and two or more rotary valves, such as that depicted in FIG. 2. It will be understood that there could be more than two sieve chambers, such as four, six, or eight, each having a separate rotary valve to independently control the input and withdrawal of streams to the sieve chamber. The number of the absorbent beds in each sieve chamber can be equal or unequal. In one embodiment, depicted in FIG. 2, the simulated moving bed adsorption apparatus comprises two sieve chambers 1, 2, each containing 12 adsorbent beds. The flow of streams to and from first sieve chamber 1 are directed by first rotary valve 10 and the flow of streams to and from second sieve chamber 2 are directed by second rotary valve 20.

First and second sieve chambers 1 and 2 are operated independently, such that there is no fluid communication between the two chambers. Each chamber receives feed and desorbent and produces extract and raffinate, with all streams being directed to and from the chambers by their respective rotary valves. A $C_8$ aromatic feed stream 202 is provided to the apparatus, where it is split into sub-streams, with first feed sub-stream 212 being introduced to first sieve chamber 1 by first rotary valve 10 and second feed sub-stream 222 being introduced to second sieve chamber 2 by second rotary valve 20. Desorbent 204 is provided to the apparatus, where it is split into sub-streams, with first desorbent sub-stream 214 being introduced to first sieve chamber 1 by first rotary valve 10 and second desorbent sub-stream 224 being introduced to second sieve chamber 2 by second rotary valve 20. First extract sub-stream 216 is withdrawn from first sieve chamber 1 by first rotary valve 10 and second extract sub-stream 226 is withdrawn from second sieve chamber 2 by second rotary valve 20, and the first and second extract sub-streams are combined to produce extract stream 206 for downstream processing. First raffinate sub-stream 218 is withdrawn from first sieve chamber 1 by first rotary valve 10 and second raffinate sub-stream 228 is withdrawn from second sieve chamber 2 by second rotary valve 20, and the first and second raffinate sub-streams are combined to produce raffinate stream 208 for downstream processing.

Throughout the process, a flow of circulating fluid is maintained throughout each sieve chamber. After the step time, of duration X, the first and second rotary valves 10, 20 advance one position and the location of sub-streams into and out of the first and second sieve chambers 1, 2 are switched to a bed downstream, in terms of the circulating fluid. The first and second rotary valves 10, 20 may step simultaneously or independently in a staggered manner.

During step time X, the flow rates of at least one pair of sub-streams to or from the sieve chambers are changed. The flow rates of the feed sub-streams, desorbent sub-streams, extract sub-streams, and/or raffinate sub-streams may be varied during step time X. For example, after a first subinterval X' of step time X, the flow rates of first feed sub-stream 212 and second feed sub-stream 222 are changed. The flow rates of the desorbent, extract, and raffinate sub-streams may also change after subinterval X', or after a second subinterval X'', or after a third subinterval X'''. To minimize impact on downstream processes, the overall flow rates of the feed stream and desorbent stream to the apparatus, and the overall flow rates of the extract and raffinate streams from the apparatus, are maintained to be substantially constant. As used herein, the term "substantially constant" means a sum of flow rates of sub-streams, for example the first and second feed sub-streams 212, 222, varies within the range of ±10%, ±8%, ±5%, ±3%, or ±1%, based on the average flow rate of the overall stream during the process.

When the flow rate of one pair of sub-streams is varied during step time X, the flow rate of the first sub-stream is varied according to a first flow rate profile and the flow rate of the second sub-stream is varied according to a second flow rate profile. When the flow rate of more than one pair of sub-streams is varied during step time X, the flow rate profiles of the first sub-streams may be the same or different and the flow rate profiles of the second sub-streams may be the same or different. In one embodiment, the flow rates of all first sub-streams are varied during step time X according to the first flow rate profile and the flow rates of all second sub-streams are varied during step time X according to the second flow rate profile. In another embodiment, the flow rate of the first feed sub-stream 212 is varied during step time X according to the first flow rate profile, the flow rate of the second feed sub-stream 222 is varied according to the second flow rate profile, the flow rate of the first extract sub-stream 216 is varied according to a third flow rate profile, the flow rate of the second extract sub-stream 226 is varied according to a fourth flow rate profile, the flow rate of the first raffinate sub-stream 218 is varied according to a fifth flow rate profile, the flow rate of the second raffinate sub-stream 228 is varied according to a sixth flow rate profile, the flow rate of the first desorbent sub-stream 214 is varied according to a seventh flow rate profile, and the flow rate of second the desorbent sub-stream 224 is varied according to an eighth flow rate profile.

In one embodiment, the first and second flow rate profiles have an inverse relationship, such that when one sub-stream has a higher flow rate, the other sub-stream has a lower flow rate, and the sum of the flow rates of the sub-streams are substantially constant. In this embodiment, the rotary valves step simultaneously. FIG. 3 shows an example profile according to this embodiment.

Figure 3A:
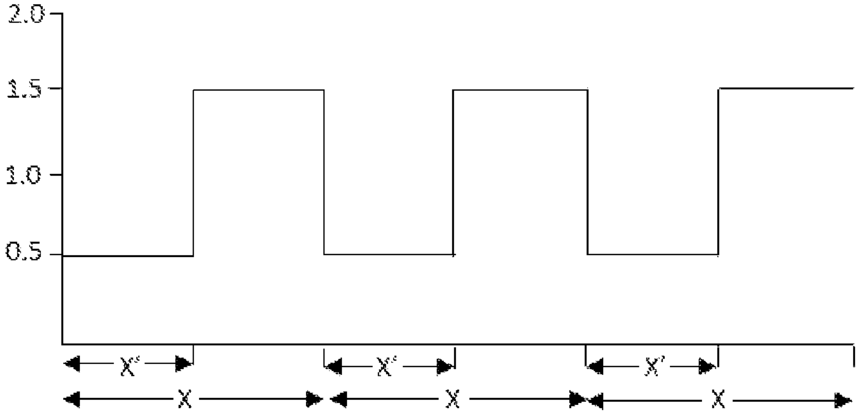
FIGS. 3A and 3B show flow rate profiles of feed sub-streams according to an embodiment related to the embodiment illustrated in FIG. 2.
Figure 3B:
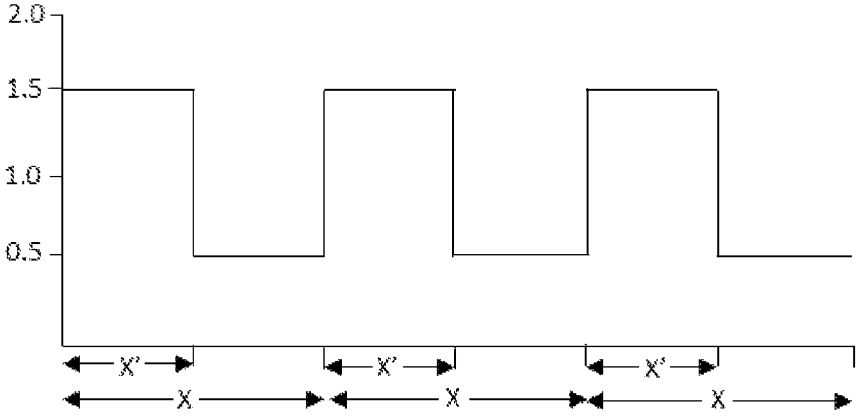

Referring now to FIG. 3 and with continuing reference to FIG. 2, the flow rate of the feed sub-streams 212, 222 are changed during step time X and the overall flow rate of the feed stream to the simulated moving bed apparatus is held substantially constant at about 2 $m^3$/min. FIG. 3A shows the flow rate profile of first feed sub-stream 212 from first rotary valve 10 into first sieve chamber 1. FIG. 3B shows the flow rate profile of second feed sub-stream 222 from second rotary valve 20 into second sieve chamber 2. During subinterval X' of step time X, the flow rate of first feed sub-stream 212 is held constant at about 0.5 $m^3$/min and the flow rate of second feed sub-stream 222 is held constant at about 1.5 $m^3$/min. After subinterval X', the flow rate of first feed sub-stream 212 is changed to about 1.5 $m^3$/min and held constant for the remainder of step time X. Also at subinterval X', the flow rate of second feed sub-stream 222 is changed to about 0.5 $m^3$/min and held constant for the remainder of step time X. At the end of step time X, the rotary valves step one bed downstream and the process repeats.

Subinterval X' is less than the step time X, for example less than 80% of X, such as from 20 to 80% of X, from 20 to 60% of X, from 30 to 60% of X, from 30 to 50%, or about 50% of step time X. In some embodiments, subinterval X' can be ½X, ⅓X, ¼X, ¾X, ⅕X, ⅖X, ⅗X, ⅘X, and if X is 60 seconds, X' can be 12, 15, 20, 24, 30, 36, 45, or 48 seconds of step time X. In a practical embodiment, X is divided into a number of subintervals equal to the number of sieve chambers in the apparatus. Thus, if there are two sieve chambers, X' is ½X, if there are three sieve chambers, X' is ⅓X, and so on.

FIG. 3 depicts an example profile only and should not be read as limiting. The flow rates of the desorbent sub-streams, extract sub-streams, and raffinate sub-streams may alternatively or additionally be varied during step time X. The flow rate profiles of each stream that is varied may be the same or different. In embodiments in which the flow rate profiles are different, the flow rate profiles of each corresponding stream have an inverse relationship. That is, if the flow rate of the first extract sub-stream 216 is varied according to a third flow rate profile and the flow rate of the second extract sub-stream 226 is varied according to a fourth flow rate profile, the third and fourth flow rate profiles have an inverse relationship. Also, if the flow rate of the first raffinate sub-stream 218 is varied according to a fifth flow rate profile and the flow rate of the second raffinate sub-stream 228 is varied according to a sixth flow rate profile, the fifth and sixth flow rate profiles have an inverse relationship, and if the flow rate of the first desorbent sub-stream 214 is varied according to a seventh flow rate profile and the flow rate of second the desorbent sub-stream 224 is varied according to an eighth flow rate profile, the seventh and eighth flow rate profiles have an inverse relationship. The overall flow rate of each stream to or from the apparatus may be the same or different. There may be multiple changes of flow rates of sub-streams during step time X. As long as the flow rates of the sub-streams are varied in such a manner that the overall flow rate of the combined sub-streams is substantially constant, the other variables may be manipulated according to one skilled in the art.

Figure 4A:
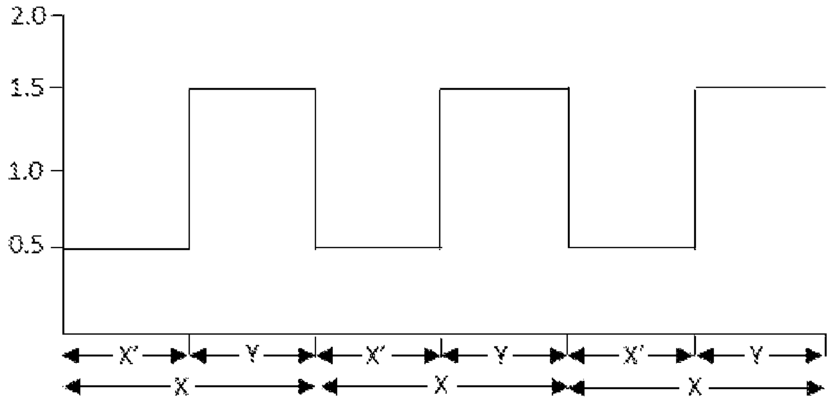
FIGS. 4A and 4B show flow rate profiles of feed sub-streams according to an embodiment related to the embodiment illustrated in FIG. 2.
Figure 4B:
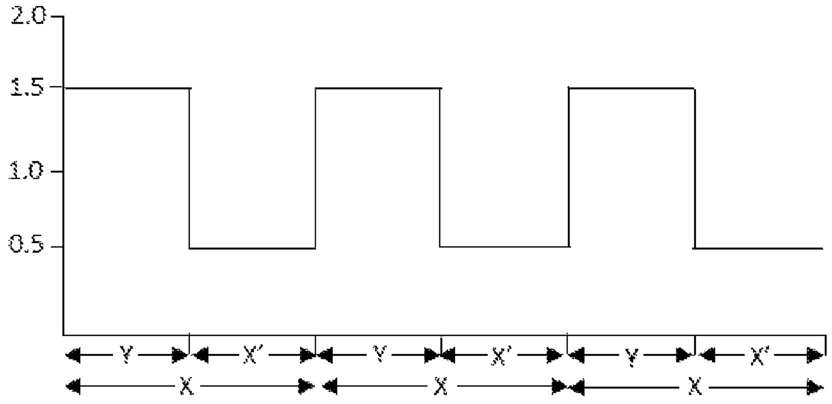

In another embodiment, the first and second flow rates profiles are the same, but the first and second rotary valves are off-set and step in a staggered manner so that the overall flow rate of the combined sub-streams to or from the apparatus is substantially constant. FIG. 4 shows an example profile according to this embodiment. In FIG. 4 and with continuing reference to FIG. 2, the flow rates of the feed sub-streams 212, 222 are changed during step time X and the overall flow rate of the feed stream to the simulated moving bed apparatus is held substantially constant at about 2 $m^3$/min. FIG. 4A shows the profile of the flow rate of first feed sub-stream 212 from first rotary valve 10 into first sieve chamber 1. FIG. 4B shows the profile of the flow rate of second feed sub-stream 222 from second rotary valve 20 into second sieve chamber 2. During subinterval X' of step time X, the flow rate of first and second feed sub-streams 212, 222 is held constant at about 0.5 $m^3$/min. After subinterval X', the flow rate of first and second feed sub-streams 212, 222 is changed to about 1.5 $m^3$/min and held constant for the remainder of step time X, hereinafter referred to as subinterval Y. However, the rotary valves are off-set such that while first rotary valve 10 is in subinterval X', directing first feed sub-stream 212 at a flow rate of 0.5 $m^3$/min, second rotary valve 20 is in subinterval Y, directing second feed sub-stream 222 at a flow rate of 1.5 $m^3$/min. At the end of step time X, each rotary valve steps one bed downstream and the process repeats. Due to the rotary valves being off-set, each rotary valves steps after subinterval X' of the other rotary valve.

Again, FIG. 4 depicts an example profile only and should not be read as limiting. The flow rates of the desorbent sub-streams 214, 224, extract sub-streams 216, 226, and raffinate sub-streams 218, 228 may alternatively or additionally be varied during step time X. The flow rate profiles of each stream that is varied may be the same or different, but is preferably the same. The overall flow rate of each stream may be the same or different. There may be multiple changes of flow rates of sub-streams during step time X. As long as the flow rates of the sub-streams are varied and the rotary valves step in such a manner that the overall flow rate of the combined sub-streams is substantially constant, the other variables may be manipulated according to one skilled in the art.

In a preferred embodiment, the sub-streams have identical flow rate profiles and the rotary valves are off-set with staggered stepping. Using the same flow rate profile for each sieve chamber allows for full optimization of the PowerFeed process in both chambers simultaneously, while also achieving the benefit of substantially constant flow to minimize the size of and strain on peripheral equipment.

The following description relates to variation of flows of streams into and out of a first sieve chamber. The variation of flows of streams into and out of the second or other sieve chambers can be same or different, as described above, and will become apparent to one of ordinary skill in the art, in particular when a substantially constant overall flow rate of feed stream 202, and/or desorbent stream 204, and/or extract stream 206, and/or raffinate stream 208 is sought to be maintained, and therefor is omitted herein.

In some embodiments the first feed sub-stream 212 into and out of the first sieve chamber 1 may be varied at least once during step time X. At the beginning of step time X, the flow rates may be held constant for a subinterval X' of step time X. After the expiration of subinterval X' of step time X, the flow rate of the first feed sub-stream 212 may be changed. Step time X may be split into at least two subintervals. The durations of each of the subintervals may be the same or different.

In some embodiments, more of the first feed sub-stream 212 may be introduced into the first sieve chamber 1 during the latter portion of step time X than in the earlier portion of step time X. For example, if X is 60 seconds, the bed into which the flow of first feed sub-stream 212 is introduced is switched every 60 seconds, and less of the first feed sub-stream 212 introduced during the 60 seconds would be introduced during the first 30 seconds of X than is introduced during the last 30 seconds of X.

In some embodiments, less than 30% of the first feed sub-stream 212 may be introduced into the first sieve chamber during subinterval X', which is from 0 to 40% of X (i.e., a time interval extending over the first 40% of X), and at least 70% of the first feed sub-stream 212 may be introduced into the first sieve chamber during the remaining portion of X, which is from 40 to 100% of X (i.e., a time interval extending from the end of the first 40% of X to the end of X). According to this embodiment, if X is 60 seconds, less than 30% of the first feed sub-stream 212 would be introduced into the first sieve chamber during the first 24 seconds of X, and at least 70% of the first feed sub-stream 212 introduced during the 60 seconds may be introduced during the last 36 seconds of X.

In another embodiment, the flow of the first feed sub-stream 212 may be described in terms of five (5) subintervals of X. In particular, (1) less than 10% of the first feed sub-stream 212, which is introduced in step time X, may be introduced during a time subinterval of from 0 to 20% of X (i.e., a time interval extending over the first 20% of X), (2) less than 15% of the first feed sub-stream 212, which is introduced in step time X, may be introduced during a time subinterval of from 20 to 40% of X (i.e., a time interval extending from the end of the first 20% of X to the end of the first 40% of X), (3) at least 15% of the first feed sub-stream 212, which is introduced in step time X, may be introduced during a time subinterval of from 40 to 60% of X (i.e., a time interval extending from the end of the first 40% of X to the end of the first 60% of X), (4) at least 20% of the first feed sub-stream 212, which is introduced in step time X, may be introduced during a time subinterval of from 60 to 80% of X (i.e., a time interval extending from the end of the first 60% of X to the end of the first 80% of X), and (5) at least 20% of the first feed sub-stream 212, which is introduced in step time X, may be introduced during a time subinterval of from 80 to 100% of X (i.e., a time interval extending from the end of the first 80% of X to the end of X). According to this embodiment, if X is 60 seconds, (1) less than 10% of the first feed sub-stream 212, which is introduced during the 60 seconds, would be introduced during the first 12 seconds; (2) less than 15% of the first feed sub-stream 212, which is introduced during the 60 seconds, would be introduced during a time subinterval of from 12 to 24 seconds from the start of X; (3) at least 15% of the first feed sub-stream 212, which is introduced during the 60 seconds, would be introduced during a time subinterval of from 24 to 36 seconds from the start of X, (4) at least 20% of the first feed sub-stream 212, which is introduced in step time X, would be introduced during a time subinterval of from 36 to 48 seconds from the start of X, and (5) at least 20% of the first feed sub-stream 212, which is introduced during the 60 seconds, would be introduced during a time subinterval of from 48 to 60 seconds from the start of X. After 60 seconds the flow of first feed sub-stream 212 to a bed would be interrupted and resumed in the next bed downstream in terms of the flow of circulating fluid in the first sieve chamber.

The flow rate of other sub-streams may also be varied during step time X. For example, less of the first raffinate sub-stream 218 may be withdrawn from the first sieve chamber 1 during the latter portion of step time X than in the earlier portion of step time X. For example, if X is 60 seconds, the flow of the first raffinate sub-stream 218 from a bed of the first sieve chamber is switched to a bed downstream every 60 seconds, and less of the first raffinate sub-stream 218 withdrawn during the 60 seconds would be withdrawn during the last 30 seconds of X than that withdrawn during the first 30 seconds of X.

In a particular embodiment, at least 60% of the first raffinate sub-stream 218 may be withdrawn from the first sieve chamber 1 during a time subinterval of from 0 to 40% of X, and less than 40% of the first raffinate sub-stream 218 may be withdrawn from the first sieve chamber during a time subinterval of from 40 to 100% of X. According to this embodiment, if X is 60 seconds, at least 60% of the first raffinate sub-stream 218 would be withdrawn from the first sieve chamber during the first 24 seconds of X, and less than 40% of the first raffinate sub-stream 218 may be withdrawn from the first sieve chamber during the last 36 seconds of X.

In another embodiment, the flow of first raffinate sub-stream 218 may be described in terms of five (5) subintervals of X. In particular, (1) at least 25% of the first raffinate sub-stream 218, which is withdrawn in step time X, may be withdrawn during a time subinterval of from 0 to 20% of X; (2) at least 25% of the first raffinate sub-stream 218, which is withdrawn in step time X, may be withdrawn during a time subinterval of from 20 to 40% of X; (3) less than 15% of the first raffinate sub-stream 218, which is withdrawn in step time X, may be withdrawn during a time subinterval of from 40 to 60% of X; (4) less than 15% of the first raffinate sub-stream 218, which is withdrawn in step time X, may be withdrawn during a time subinterval of from 60 to 80% of X; and (5) less than 20% of the first raffinate sub-stream 218, which is withdrawn in step time X, may be withdrawn during a time subinterval of from 80 to 100% of X. According to this embodiment, if X is 60 seconds, (1) at least 25% of the first raffinate sub-stream 218, which is withdrawn in step time X, would be withdrawn during the first 12 seconds of X; (2) at least 25% of the first raffinate sub-stream 218, which is withdrawn in step time X, would be withdrawn during a time subinterval of from 12 to 24 seconds from the start of X; (3) less than 15% of the first raffinate sub-stream 218, which is withdrawn in step time X, would be withdrawn during a time subinterval of from 24 to 36 seconds from the start of X; (4) less than 15% of the first raffinate sub-stream 218, which is withdrawn in step time X, would be withdrawn during a time subinterval of from 36 to 48 seconds from the start of X, and (5) less than 15% of the first raffinate sub-stream 218, which is withdrawn in step time X, would be withdrawn during a time subinterval of from 48 to 60 seconds from the start of X. After 60 seconds the flow of first raffinate sub-stream 218 from a bed would be interrupted and resumed in the next bed downstream in terms of the flow of circulating fluid in the first sieve chamber.

The flow rate of the first extract sub-stream 216 may also be varied during step time X. For example, less than 30% of the first extract sub-stream 216 may be withdrawn from the first sieve chamber 1 during a time subinterval of from 0 to 40% of X, and at least 70% of the first extract sub-stream 216 may be withdrawn from first sieve chamber during a time subinterval of from 40 to 100% of X. According to this embodiment, if X is 60 seconds, less than 30% of the first extract sub-stream 216 would be withdrawn from the first sieve chamber during the first 20 seconds of X, and at least 70% of the first extract sub-stream 216 may be withdrawn from the first sieve chamber during the last 40 seconds of X.

In another embodiment, the flow of first extract sub-stream may be described in terms of five (5) subintervals of X. In particular, (1) less than 15% of the first extract sub-stream 216, which is withdrawn in step time X, may be withdrawn during a time subinterval of from 0 to 20% of X; (2) less than 15% of the first extract sub-stream 216, which is withdrawn in step time X, may be withdrawn during a time subinterval of from 20 to 40% of X; (3) at least 15% of the first extract sub-stream 216, which is withdrawn in step time X, may be withdrawn during a time subinterval of from 40 to 60% of X; (4) at least 20% of the first extract sub-stream 216, which is withdrawn in step time X, may be withdrawn during a time subinterval of from 60 to 80% of X; and (5) at least 20% of the first extract sub-stream 216, which is withdrawn in step time X, may be withdrawn during a time subinterval of from 80 to 100% of X. According to this embodiment, if X is 60 seconds, (1) less than 15% of the first extract sub-stream 216, which is withdrawn in step time X, would be withdrawn during the first 12 seconds of X; (2) less than 15% of the first extract sub-stream 216, which is withdrawn in step time X, would be withdrawn during a time subinterval of from 12 to 24 seconds from the start of X; (3) at least 15% of the first extract sub-stream 216, which is withdrawn in step time X, would be withdrawn during a time subinterval of from 24 to 36 seconds from the start of X; (4) at least 20% of first extract sub-stream 216, which is withdrawn in step time X, would be withdrawn during a time subinterval of from 36 to 48 seconds from the start of X, and (5) at least 20% of the first extract sub-stream 216, which is withdrawn in step time X, would be withdrawn during a time subinterval of from 48 to 60 seconds from the start of X. After 60 seconds the flow of the first extract sub-stream 216 from a bed would be interrupted and resumed in the next bed downstream in terms of the flow of circulating fluid in the s first sieve chamber.

The extract sub-streams 216, 226 withdrawn from each sieve chamber 1, 2, respectively, may comprise at least 50, 75, 90, 99, or 99.7 volume percent of paraxylene, based on the total volume of xylenes and ethylbenzene present in the corresponding extract sub-stream. The extract sub-streams 216, 226 are withdrawn from the sieve chambers through conduits connected to rotary valves 10, 20, respectively. After the extract sub-streams 216, 226 are passed through the rotary valves 10, 20, respectively, they are combined to form an extract stream 206, which can then be subsequently separated by distillation downstream to provide a purified paraxylene product and a desorbent-rich stream. The purified paraxylene product may be recovered and the desorbent-rich stream may be recycled to for re-use in the simulated moving bed adsorptive process.

The raffinate sub-streams 218, 228 withdrawn from each sieve chamber 1, 2, respectively, may comprise desorbent, metaxylene, orthoxylene and ethylbenzene. Raffinate sub-streams 218, 228, are withdrawn from the sieve chamber 1, 2, respectively, through conduits connected to rotary valves 10, 20, respectively. After the raffinate sub-streams 218, 228, are passed through the rotary valves 10, 20, respectively, they can be combined to form a raffinate stream 208. The bed, from which the raffinate sub-stream 218, 228 is withdrawn, is downstream, based on the direction of the flow of circulating fluid, from the bed into which feed sub-stream 212, 222, respectively, is introduced. The raffinate stream 208 then may be distilled to obtain a desorbent-rich stream and a stream enriched in $C_8$ aromatics comprising metaxylene, orthoxylene and ethylbenzene. The desorbent-rich stream may be recycled for re-use in the simulated moving bed adsorptive process. The stream enriched in $C_8$ aromatics may be isomerized in the liquid phase, vapor phase, or a combination thereof. In particular, these $C_8$ aromatics may be passed to an isomerization unit to obtain an isomerized product stream comprising from 15 to 30 volume percent, for example, from 20 to 30 volume percent of paraxylene. The isomerized product stream may then be recycled to the simulated moving bed adsorptive process.

In some embodiments, at least two raffinate sub-streams are withdrawn from each of the sieve chambers. An ethylbenzene-rich raffinate sub-stream may comprise ethylbenzene and desorbent, and a xylene isomer-rich raffinate sub-stream may comprise orthoxylene, metaxylene and desorbent. When the process adopts two sieve chambers, a first ethylbenzene-rich raffinate sub-stream withdrawn from the first sieve chamber can be combined with a second ethylbenzene-rich raffinate sub-stream withdrawn from the second sieve chamber to form an ethylbenzene-rich raffinate stream, which then may be distilled to obtain a desorbent-rich stream and an ethylbenzene-rich stream. The ethylbenzene-rich stream may be subjected to ethylbenzene isomerization conducted in the vapor phase, ethylbenzene dealkylation conducted in the vapor phase, or purged to fuel gas. The desorbent-rich stream may be recycled to the process. Likewise, a first xylene isomer-rich raffinate sub-stream withdrawn from the first sieve chamber can be combined with a second xylene isomer-rich raffinate sub-stream to form an isomer-rich raffinate stream, which then may be distilled to obtain a desorbent-rich stream and a xylene isomer-rich stream. The desorbent-rich stream may be recycled and the xylene isomer-rich stream may be isomerized, for example in the liquid phase, and recycled to the simulated moving bed adsorptive apparatus.

Various embodiments have been described above with reference to specific details which, it will be understood by one of ordinary skill in the art, are intended to exemplary and not limiting. Accordingly, embodiments according to this disclosure can be practiced other than as specifically set forth herein.

EXAMPLES

In the following examples, a computer model is used to simulate separation of paraxylene from other $C_8$ aromatics in a Parex™ unit. In each comparative example, a simulated moving bed apparatus having 24 adsorptive beds like that in a commercial Parex™ unit is used. In each inventive example, a simulated moving bed apparatus having two sieve chambers, A and B, each having 12 adsorptive beds is used. A mixture of xylenes (paraxylene (PX), orthoxylene (OX), metaxylene (MX), and ethylbenzene (EB)) and desorbent (para-diethyl benzene (PDEB)) is simulated as streams introduced to the unit.

In each comparative example, the zone configuration is fixed as 6:9:6:3, i.e., six beds between the desorbent and extract streams, nine beds between extract and feed streams, six beds between feed and raffinate streams, and three bed between raffinate and desorbent streams. The flow rates of feed, extract, raffinate and desorbent introduced and withdrawn during each step time are kept constant.

In each inventive example, the zone configuration is fixed as 3:4:3:2 in first sieve chamber A and a second sieve chamber B, respectively, i.e., three beds between the desorbent and extract streams, four beds between extract and feed streams, three beds between feed and raffinate streams, and two bed between raffinate and desorbent streams. The feed stream is split into a first feed sub-stream, which is introduced into the first sieve chamber ("chamber A") via a first rotary valve, and a second feed sub-stream, which is introduced into the second sieve chamber ("chamber B") via a second rotary valve. In each inventive example, locations of sub-streams in and out of the sieve chambers A and B are switched downstream in terms of the direction of the circulating fluid after a step time X. The first and second rotary valves are off-set by a time interval X'. In each inventive example, X' is 50% of X. Thus, the first rotary valve switches the locations of sub-streams to and from sieve chamber A, and then, after 50% of X, the second rotary valve switches the locations of sub-streams to or from sieve chamber B. PowerFeed is used in each inventive example as shown below.

The following assumptions were made in accordance with "Modeling and Simulation of a Simulated Moving Bed for the Separation of P-Xylene", M. Minceva, and A. E. Rodrigues, *Industrial & Engineering Chemistry Research,* 41 (2002), page 3454-61: (1) isothermal, isobaric operation; (2) constant velocity within each zone; (3) solid phase concentration is homogeneous throughout adsorbent particles; and (4) the mass transfer between the liquid and adsorbent phases is described by the linear driving force (LDF) model. Based on the above assumptions, mass balance equations were written as:

$$\frac{\partial C_{ik}(z,t)}{\partial t} = \mathcal{D}_{Lk}(t)\frac{\partial^2 C_{ik}(z,t)}{\partial z^2} - v_k^*(t)\frac{\partial C_{ik}(z,t)}{\partial z} - \frac{(1-\varepsilon)}{\varepsilon}\frac{\partial q_{ik}(z,t)}{\partial t}$$

where i is the index for components (i=PX, MX, OX, EB, PDEB); k is the index for columns (k=1 . . . $N_{bed}$, where $N_{bed}$ is the total number of beds); C is the bulk liquid concentration $$\left(\text{unit } \frac{\text{kg}}{\text{m}^3}\right);$$

q is the sorbate concentration $$\left(\text{unit } \frac{\text{kg}}{\text{m}^3}\right);$$

$\epsilon$ is the overall porosity; D is the axial dispersion coefficient; and $v^*_k$ is the interstitial velocity in columns.

The mass balance equation describes the change of bulk liquid concentration at a specific position inside of a column (first term) with respect to dispersion (second term), convection (third term), and adsorption/desorption process (fourth term).

The LDF model was written as:

$$\frac{\partial q_{ik}(z,t)}{\partial t} = k(q_{ik}^*(z,t) - q_{ik}(z,t))$$

where q* is the adsorbate concentration in equilibrium with the liquid phase $$\left(\text{unit } \frac{\text{kg}}{\text{m}^3}\right).$$

The LDF model describes the mass flux into the solid phase. The adsorbate concentration in equilibrium with the liquid phase can be obtained from an adsorption isotherm.

At the node between columns, the mass balance is calculated by subtracting outlet flow rates and adding inlet flow rates:

$$F_{k+1}=F_k+F_{Feed,k}+F_{desorbent,k}-F_{raffinate,k}-F_{extract,k}.$$

For columns that are not connected to inlet or outlet streams, $F_{Feed,k}$ or $F_{desorbent,k}$ or $F_{raffinate,k}$ or $F_{extract,k}$ is zero.

The dynamics of the SMB system reaches a cyclic steady state (CSS) where the concentration profiles in a bed at the beginning of the step are exactly identical to the concentration profiles in the next bed at the end of the step. These CSS constraints are given as:

$$C_{k+1}(z,t_{end})=C_k(z,t_0)$$

where $t_{end}$ is the time at the end of a step, and to is the beginning of a step. Here, stepwise symmetry is assumed, where every step is identical.

Model parameters were taken from the literature, in particular, from M. Minceva, and A. E. Rodrigues, 'Modeling and Simulation of a Simulated Moving Bed for the Separation of P-Xylene', *Industrial & Engineering Chemistry Research,* 41 (2002), 3454-61. Model parameters are summarized in Table 1, in which $L_c$ refers to column length; $d_c$ refers to column diameter; $V_c$ refers to column volume; $P_e$ refers to Peclet number; k refers to mass transfer coefficient; $d_p$ refers to particle diameter; $\epsilon$ refers to bed porosity; ρ refers to density; $q_{mPX(MX;OX;EB)}$ and $q_{mPDEB}$ refer to adsorbed phase saturation concentration of the components; $K_{PX}$, $K_{MX}$, $K_{OX}$, $K_{EB}$, and $K_{PDEB}$ refer to adsorption equilibrium constant of PX, MX, OX, EB, and PDEB, respectively.

TABLE 1

| SMB unit Geometry | Model Parameter |
|---|---|
| $L_c$ = 113.5 cm | $P_e = v_k L_k/D_{Lk}$ = 2000 |
| $d_c$ = 411.7 cm | k = 2 $min^{-1}$ |
| $V_c$ = 15.1 × $10^6$ $cm^3$ | $d_p$ = 0.092 cm |
| No. of Columns = 24 | $\epsilon$ = 0.39 |
| Configuration = 6-9-6-3 | ρ = 1.39 g/$cm^3$ |
| | $q_{mPX(MX;\ OX;\ EB)}$ = 130.3 mg/g |
| | $K_{PX}$ = 1.0658 $cm^3$/mg |
| | $K_{MX}$ = 0.2299 $cm^3$/mg |
| | $K_{OX}$ = 0.1884 $cm^3$/mg |
| | $K_{EB}$ = 0.3067 $cm^3$/mg |
| | $q_{mPDEB}$ = 107.7 mg/g |
| | $K_{PDEB}$ = 1.2935 $cm^3$/mg |

The mass transfer coefficient was changed from 2 $min^{-1}$ to 0.75 $min^{-1}$.

In each inventive example, there was a different objective function for the optimization object as indicated. The remainder of the optimization object for each inventive example was formulated as follows:

Decision variables: $F_1$, $F_2$, $F_3$, $F_4$, $t_{st}$ where $F_j$'s are zone flow rates, and $t_{st}$ is the step time, Main Constraint: Extract purity (PX)≥99.7%

Extract recovery (PX)≥97.0%.

The model was discretized into a set of algebraic differential equations by applying the center finite difference method (CFDM) to the spatial domain and orthogonal collocation finite element method (OCFEM) to the temporal domain respectively. The discretized problem was solved by an interior-point optimization algorithm (IPOPT).

Example 1 (Comparative)

The flow rates and results for this simulation are shown in Table 2.

TABLE 2

| Operation conditions | 0 - X |
|---|---|
| Feed flow rate ($m^3$/min) | 3.83 |
| Desorbent flow rate ($m^3$/min) | 4.61 |
| Extract flow rate ($m^3$/min) | 3.83 |
| Raffinate flow rate ($m^3$/min) | 4.61 |
| SMB Performance parameters | |
| Throughput ($m^3$/min) | 3.83 |
| Desorbent to feed ratio | 1.2 |

This simulation shows that for an optimized 24-bed conventional simulated moving bed unit, the throughput is 3.83 $m^3$/min.

Example 2 (Inventive)

In this inventive example, the objective function is to maximize $F_{Feed}$, the feed flow rate. The flow rates and results for the simulation of Example 2 are shown in Table 3.

TABLE 3

| | 0 - X/2 | | | X/2 - X | | |
|---|---|---|---|---|---|---|
| Operating conditions | Chamber A | Chamber B | Total | Chamber A | Chamber B | Total |
| Feed sub-stream flow rate ($m^3$/min) | 0 | 6.11 | 6.11 | 6.11 | 0 | 6.11 |
| Desorbent sub-stream flow rate ($m^3$/min) | 4.88 | 2.45 | 7.33 | 2.45 | 4.88 | 7.33 |
| Extract sub-stream flow rate ($m^3$/min) | 0 | 5.8 | 5.8 | 5.8 | 0 | 5.8 |
| Raffinate sub-stream flow rate ($m^3$/min) | 4.88 | 2.77 | 7.65 | 2.77 | 4.88 | 7.65 |
| SMB Performance parameters | | | | | | |
| Throughput ($m^3$/min) | | | 6.12 | | | |
| Ratio of Desorbent to Feed flow rate | | | 1.2 | | | |

This simulation shows that for an optimized simulated moving bed unit, with two sieve chambers each having 12 beds, operated independently and with PowerFeed, the combined throughput is 6.2 $m^3$/min. Thus, the two-chamber configuration is able to achieve a 60% improvement in the throughput, while using the same desorbent to feed ratio of 1.2. The total flow, which is the sum of the flows from both chambers is constant for all feed and product streams.

Example 3 (Comparative)

In this comparative example, the throughput is fixed to 3.8 $m^3$/min and the unit is optimized to minimize the amount of desorbent being used. The flow rates and results for this simulation are shown in Table 4.

TABLE 4

| Operation conditions | 0 - X |
|---|---|
| Zone 1 flow rate ($m^3$/min) | 6.16 |
| Feed flow rate ($m^3$/min) | 3.8 |
| Desorbent flow rate ($m^3$/min) | 2.08 |
| Extract flow rate ($m^3$/min) | 1.46 |
| Raffinate flow rate ($m^3$/min) | 4.42 |
| SMB Performance parameters | |
| Throughput ($m^3$/min) | 3.8 |
| Desorbent to Feed ratio | 0.55 |

As shown in Table 4, the conventional 24-bed SMB unit requires a desorbent to feed ratio of 0.55 to maintain the desired throughput.

Example 4 (Inventive)

In this inventive example, the objective function is to minimize the amount of desorbent being used, while maintaining a fixed throughput of 3.8 $m^3$/min. The flow rates and results for the simulation of Example 4 are shown in Table 5. Zone 1 flow rate refers to the sum of flow rates of the recycled flow from the last bed and the desorbent.

TABLE 5

| | 0 - X/2 | | | X/2 - X | | |
|---|---|---|---|---|---|---|
| Operating conditions | Chamber A | Chamber B | Total | Chamber A | Chamber B | Total |
| Zone 1 flow rate ($m^3$/min) | 3.37 | 3.23 | 6.6 | 3.23 | 3.37 | 6.6 |
| Feed sub-stream flow rate ($m^3$/min) | 2.28 | 1.52 | 3.8 | 1.52 | 2.28 | 3.8 |
| Desorbent sub-stream flow rate ($m^3$/min) | 0.3 | 1.68 | 1.98 | 1.68 | 0.3 | 1.98 |
| Extract sub-stream flow rate ($m^3$/min) | 1.39 | 0 | 1.39 | 0 | 1.39 | 1.39 |
| Raffinate sub-stream flow rate ($m^3$/min) | 1.19 | 3.2 | 4.39 | 3.2 | 1.19 | 4.39 |
| SMB performance parameters | | | | | | |
| Throughput ($m^3$/min) | | | 3.8 | | | |
| Ratio of Desorbent to Feed flow rate | | | 0.52 | | | |

This simulation shows that for an optimized simulated moving bed unit, with two sieve chambers each having 12 beds, operated independently and with PowerFeed, the same production rate may be achieved with a reduced desorbent to feed ratio of 0.52. In situations where desorbent is limited, this approach can reduce the operating costs of the system without reducing production rate.

Example 5 (Inventive)

In this inventive example, the objective function is to maximize Freed, the feed flow rate. The flow rates and results for the simulation of Example 2 are shown in Table 3.

TABLE 6

| Operating conditions | 0 - X/2 Chamber A | Chamber B | Total | X/2 - X Chamber A | Chamber B | Total |
|---|---|---|---|---|---|---|
| Zone 1 flow rate ($m^3$/min) | 8.5 | 8.5 | 17 | 8.5 | 8.5 | 17 |
| Feed sub-stream flow rate ($m^3$/min) | 0 | 6.3 | 6.3 | 6.3 | 0 | 6.3 |
| Desorbent sub-stream flow rate ($m^3$/min) | 5.78 | 2.69 | 8.47 | 2.69 | 5.78 | 8.47 |
| Extract sub-stream flow rate ($m^3$/min) | 0 | 6.8 | 6.8 | 6.8 | 0 | 6.8 |
| Raffinate sub-stream flow rate ($m^3$/min) | 5.78 | 2.19 | 7.97 | 2.19 | 5.78 | 7.97 |
| SMB Performance parameters | | | | | | |
| Throughput ($m^3$/min) | | | | 6.3 | | |
| Ratio of Desorbent to Feed flow rate | | | | 1.34 | | |

This simulation shows that for an optimized simulated moving bed unit, with two sieve chambers each having 12 beds, operated independently and with PowerFeed, the combined throughput is 6.3 $m^3$/min.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while various embodiments have been illustrated and described, various modifications can be made without departing from the spirit and scope of this disclosure. Accordingly, it is not intended that the invention be limited thereby. Likewise in the description above, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa. In the following claims, the recitation of identifiers (a), (b), (c), etc. before the steps of a claimed method are not intended to and therefore do not specify a particular order to the steps.

The invention claimed is:

1. A process for separating paraxylene from a mixture comprising $C_8$ aromatics by a simulated moving bed adsorption apparatus comprising at least a first sieve chamber and a second sieve chamber, each sieve chamber comprising multiple adsorbent beds, said process comprising the steps of:

(a) splitting a feed stream of the mixture into a first feed sub-stream and a second feed sub-stream, and introducing the first feed sub-stream into the first sieve chamber and the second feed sub-stream into the second sieve chamber;

(b) splitting a desorbent stream into a first desorbent sub-stream and a second desorbent sub-stream, and introducing the first desorbent sub-stream into the first sieve chamber and the second desorbent sub-stream into the second sieve chamber;

(c) withdrawing a first extract sub-stream from the first sieve chamber and a second extract sub-stream from the second sieve chamber, the first and the second extract sub-streams each comprising paraxylene and desorbent, and combining the first and the second extract sub-streams to form an extract stream;

(d) withdrawing a first raffinate sub-stream from the first sieve chamber and a second raffinate sub-stream from the second sieve chamber, the first and second raffinate sub-streams each comprising non-paraxylene $C_8$ aromatics and desorbent, and combining the first and second raffinate sub-streams to form a raffinate stream;

(e) maintaining a flow throughout the first sieve chamber;

(f) maintaining a flow throughout the second sieve chamber, wherein there is no fluid communication between the first and second sieve chambers; and (g) switching the location of sub-streams into and out of the first sieve chamber and second sieve chamber to a bed downstream in terms of the direction of the circulating fluid after a step time X;

wherein the flow rate of at least one pair of streams selected from the group consisting of the first and second feed sub-streams of (a), the first and second desorbent sub-streams of (b), the first and second extract sub-streams of (c), and the first and second raffinate sub-streams of (d) to or from the first and second sieve chambers are varied during the step time X; and wherein the flow rates of the at least one pair of sub-streams are balanced such that the flow rate of the feed stream of (a), the desorbent stream of (b), extract stream of (c), and the raffinate stream of (d) to and from the simulated moving bed adsorption apparatus is substantially constant.

2. The process of claim 1, wherein the flows of the first feed sub-stream of (a), the first desorbent sub-stream of (b), the first extract sub-stream of (c), and the first raffinate sub-stream of (d) to or from the first sieve chamber are controlled by a first rotary valve;

wherein the flows of the second feed sub-stream of (a), the second desorbent sub-stream of (b), the second extract sub-stream of (c), and the second raffinate sub-stream of (d) to or from the second sieve chamber are controlled by a second rotary valve;

wherein the flow rate of the first sub-stream is varied according to a first flow rate profile and the flow rate of the second sub-stream is varied according to a second flow rate profile, wherein the first and second flow rate profiles are the same, wherein the flow rate of at least one of the pair of streams selected from the group consisting of the first and second feed sub-streams of step (a), first and second desorbent sub-streams of (b), the first and second extract sub-streams of (c), and the first and second raffinate sub-streams of (d) to or from the first and second sieve chambers is changed after a subinterval X' of step time X; and wherein the first rotary valve and second rotary valves are off-set by the subinterval X' and step in a staggered manner.

3. The process of claim 1, wherein the flow rates of the first and second feed sub-streams of step (a) are varied during step time X.

4. The process of claim 1, wherein the flow rate of the first sub-stream is varied according to a first flow rate profile and the flow rate of the second sub-stream is varied according to a second flow rate profile, and wherein the first and second flow rate profiles have an inverse relationship.

5. The process of claim 4, wherein the flow rates of the first and second feed sub-streams of (a) and the first and second extract sub-streams of (c) are varied during step time X, wherein the first feed sub-stream and the first extract sub-stream are varied according to the first flow rate profile and the second feed sub-stream and the second extract sub-stream are varied according to the second flow rate profile.

6. The process of claim 4, wherein the flow rates of the first and second feed sub-streams of (a) and the first and second extract sub-streams of (c) are varied during step time X, wherein the first feed sub-stream is varied according to the first flow rate profile, the second feed sub-stream is varied according to the second flow rate profile, the first extract sub-stream is varied according to a third flow rate profile, and the second extract sub-stream is varied according to a fourth flow rate profile, and wherein the third and fourth flow rate profiles have an inverse relationship.

7. The process of claim 5, further wherein the flow rates of the first and second raffinate sub-streams of (d) are varied during step time X, wherein the first raffinate sub-stream is varied according to the first flow rate profile and the second raffinate sub-stream is varied according to the second flow rate profile.

8. The process of claim 6, further wherein the flow rates of the first and second raffinate sub-streams of (d) are varied during step time X, wherein the first raffinate sub-stream is varied according to a fifth flow rate profile and the second raffinate sub-stream is varied according to a sixth flow rate profile, and wherein the fifth and sixth flow rate profiles have an inverse relationship.

9. The process of claim 7, further wherein the flow rates of the first and second desorbent sub-streams of (b) are varied during step time X, wherein the first desorbent sub-stream is varied according to the first flow rate profile and the second desorbent sub-stream is varied according to the second flow rate profile.

10. The process of claim 8, further wherein the flow rates of the first and second desorbent sub-streams of (b) are varied during step time X, wherein the first desorbent sub-stream is varied according to a seventh flow rate profile and the second desorbent sub-stream is varied according to an eighth flow rate profile, and wherein the seventh and eighth flow rate profiles have an inverse relationship.

11. The process of claim 3, wherein the subinterval X' is from 20 to 80% of X.

12. The process of claim 11, wherein the subinterval X' is about 50% of X.

13. The process of claim 1, wherein more of the first feed sub-stream is introduced into the first sieve chamber during a latter portion of step time X than in an earlier portion of step time X.

14. The process of claim 13, wherein less than 30% of the first feed sub-stream introduced during step time X is introduced into the first sieve chamber during 0 to 40% of X.

15. The process of claim 13, wherein less than 10% of the first feed sub-stream introduced during step time X is introduced into the first sieve chamber during 0 to 20% of X, wherein less than 15% of the first feed sub-stream introduced during step time X is introduced into the first sieve chamber during 20 to 40% of X;

wherein at least 15% of the first feed sub-stream introduced during step time X is introduced into the first sieve chamber during 40 to 60% of X;

wherein at least 20% of the first feed sub-stream introduced during step time X is introduced into the first sieve chamber during 60 to 80% of X; and wherein at least 20% of the first feed sub-stream introduced during step time X is introduced into the first sieve chamber during 80 to 100% of X.

16. The process of claim 1, wherein more of the first extract sub-stream is withdrawn from the first sieve chamber during the latter portion of step time X than in the earlier portion of step time X.

17. The process of claim 16, wherein less than 30% of the first extract sub-stream withdrawn during step time X is withdrawn during 0 to 40% of X.

18. The process of claim 16, wherein less than 15% of the first extract sub-stream withdrawn during step time X is withdrawn during 0 to 20% of X, wherein less than 15% of the first extract sub-stream withdrawn during step time X is withdrawn during 20 to 40% of X;

wherein at least 15% of the first extract sub-stream withdrawn during step time X is withdrawn during 40 to 60% of X;

wherein at least 20% of the first extract sub-stream withdrawn during step time X is withdrawn during 60 to 80% of X; and wherein at least 20% of the first extract sub-stream withdrawn during step time X is withdrawn during 80 to 100% of X.

19. A process for separating paraxylene from a feed stream comprising paraxylene, metaxylene, orthoxylene, and ethylbenzene by a simulated moving bed adsorptive apparatus comprising at least two sieve chambers, each sieve chamber comprising multiple beds containing adsorptive material selective for adsorption of paraxylene, said process comprising the steps of:

(a) operating the at least two sieve chambers independently such that there is no fluid communication between the sieve chambers;

(b) dividing a feed stream into feed sub-streams and introducing a feed sub-stream into each of the at least two sieve chambers;

(c) dividing a desorbent stream into desorbent sub-streams and introducing a desorbent sub-stream into each of the at least two sieve chambers;

(d) withdrawing an extract sub-stream comprising paraxylene from each of the at least two sieve chambers and combining the extract sub-streams to form an extract stream;

(e) withdrawing a raffinate sub-stream comprising metaxylene, orthoxylene, and ethylbenzene from each of the at least two sieve chambers and combining the raffinate sub-streams to form a raffinate stream; and (f) switching the locations of sub-streams into and out of the at least two sieve chambers to a bed downstream after a step time X, wherein the flow rates of the feed sub-streams to the at least two sieve chambers are varied during the step time X, and wherein the flow rates of the feed sub-streams are balanced such that the flow rate of the feed stream to the simulated moving bed adsorption apparatus is maintained to be substantially constant.

20. The process of claim 19, wherein the flow rates of the feed sub-streams are varied in an inverse manner.

21. The process of claim 19, wherein the flows of the first sub-streams, desorbent sub-streams, extract sub-streams, and raffinate sub-streams to or from each sieve chamber is controlled by a separate and independent rotary valve, wherein the flow rates of the feed sub-streams to or from the at least two sieve chambers are changed after a subinterval X' of step time X, and wherein the flow rates of the feed sub-streams are varied according to the same flow rate profile but the rotary valves are off-set to maintain the overall flow rate of the feed stream to the simulated moving bed adsorption apparatus substantially constant.

22. The process of claim 20, further comprising varying the rates of the extract sub-streams from the at least two sieve chambers during the step time X, wherein the flow rates of the extract sub-streams are varied in an inverse manner.

23. The process of claim 21, further comprising varying the rates of the extract sub-streams from the at least two sieve chambers during the step time X, wherein the flow rates of the extract sub-streams are varied according to the same flow rate profile as the feed sub-streams.

24. The process of claim 20, further comprising varying the rates of the raffinate sub-streams from the at least two sieve chambers during the step time X, wherein the flow rates of the raffinate sub-streams are varied in an inverse manner.

25. The process of claim 21, further comprising varying the rates of the raffinate sub-streams from the at least two sieve chambers during the step time X, wherein the flow rates of the raffinate sub-streams are varied according to the same flow rate profile as the feed sub-streams.

* * * * *